(12) United States Patent
Brown et al.

(10) Patent No.: US 10,166,310 B2
(45) Date of Patent: *Jan. 1, 2019

(54) COMBINATION DECONTAMINATION SYSTEM FOR TRANSPORTATION ASSETS

(71) Applicant: AEROCLAVE, LLC, Winter Park, FL (US)

(72) Inventors: Ronald D. Brown, Maitland, FL (US); Paul M. Gray, Ocoee, FL (US); James S. Amrhein, Oviedo, FL (US)

(73) Assignee: AEROCLAVE, LLC, Winter Park, FL (US)

( * ) Notice: Subject to any disclaimer, the term of this patent is extended or adjusted under 35 U.S.C. 154(b) by 332 days.

This patent is subject to a terminal disclaimer.

(21) Appl. No.: 14/881,285

(22) Filed: Oct. 13, 2015

(65) Prior Publication Data

US 2016/0250368 A1 Sep. 1, 2016

Related U.S. Application Data

(60) Provisional application No. 62/063,084, filed on Oct. 13, 2014.

(51) Int. Cl.
*A61L 2/22* (2006.01)
*A61L 2/24* (2006.01)
*A61L 2/20* (2006.01)

(52) U.S. Cl.
CPC .......... *A61L 2/22* (2013.01); *A61L 2/208* (2013.01); *A61L 2/24* (2013.01); *A61L 2202/25* (2013.01)

(58) Field of Classification Search
CPC .............. A61L 2/07; A61L 2/20; A61L 2/24
See application file for complete search history.

(56) References Cited

U.S. PATENT DOCUMENTS

| | | | |
|---|---|---|---|
| 6,564,699 B1 * | 5/2003 | Vincente | A21C 13/00 165/267 |
| 7,901,618 B2 | 3/2011 | McVey et al. | |
| 8,128,888 B2 | 3/2012 | Bacik et al. | |
| 2005/0074359 A1 | 4/2005 | Krieger et al. | |
| 2016/0166721 A1 * | 6/2016 | Brown | A61L 2/07 422/26 |

FOREIGN PATENT DOCUMENTS

WO 2008/104085 9/2008

* cited by examiner

*Primary Examiner* — Sean E Conley
(74) *Attorney, Agent, or Firm* — Robert L. Wolter; Beusse, Wolter, Sanks & Maire PLLC (57) ABSTRACT

A decontamination system (10), including: a plurality of interconnected and insulated panels (18) configured to form walls (14) and a roof (16) and to define an interior (24) of an enclosure (12) configured to enclose a transportation asset; a humidifying module (30) in fluid communication with the interior of the enclosure and configured to raise a temperature and a humidity of the interior of the enclosure to a predetermined temperature level and a predetermined humidity level for a timed duration; and a dehumidifying module (50) in fluid communication with the interior of the enclosure and configured to lower the temperature and the humidity of the interior of the enclosure from the predetermined temperature level and the predetermined humidity level to ambient levels.

20 Claims, 7 Drawing Sheets

COMBINATION DECONTAMINATION SYSTEM FOR TRANSPORTATION ASSETS

This application claims benefit of the Oct. 13, 2014 filing date of application 62/063,084 which is incorporated by reference herein.

STATEMENT OF GOVERNMENT INTEREST

This invention was made with government support under Contract No. A865014C6518 awarded by the Department of Defense. The government has certain rights in the invention.

FIELD OF THE INVENTION

The present invention relates generally to a modular decontamination system capable of both biothermal decontamination and aqueous solution decontamination.

BACKGROUND OF THE INVENTION

Several types of decontamination systems employing various decontamination methods have been developed to decontaminate transportation assets such as, for example, vehicles, fixed and rotary wing aircraft, and rail cars etc. An aqueous decontamination system may apply a liquid decontaminant such as hydrogen peroxide to surfaces of concern to render the contaminant harmless. Aqueous decontamination systems often require hand application of the aqueous disinfectant, or may only apply the aqueous disinfectant to the exterior or the interior of the transportation asset.

Biothermal decontamination systems may define a chamber and manipulate the environment within the chamber in a manner that is effective to render the decontaminants safe and/or more susceptible to additional decontamination treatment. Such manipulation may include raising a temperature and/or a humidity level to threshold levels for set periods of time. Often these systems are bulky and complex and/or find it difficult to maintain the desired temperature. Consequently, there remains room in the art for improvement.

BRIEF DESCRIPTION OF THE DRAWINGS

These and other advantages of the invention will become more apparent from the following description in view of the drawings. Similar structures illustrated in more than one figure are numbered consistently among the drawings.

DETAILED DESCRIPTION OF THE INVENTION

A more particular description of the invention briefly described above will be rendered by reference to specific embodiments thereof that are illustrated in the appended drawings. Understanding that these drawings depict only typical embodiments of the invention and are not therefore to be considered to be limiting of its scope, the invention will be described and explained.

The inventors have developed a decontamination system that provides both biothermal decontamination and aqueous decontamination of surfaces and spaces of transportation assets in an enclosure formed of plural, insulated, easily assembled panels. The decontamination processes reach both the exterior and the interior of the transportation asset simultaneously, and the insulative properties of the panels enables superior temperature control, such as but not limited to during biothermal decontamination. Biothermal decontamination includes raising a temperature and/or a humidity level inside the enclosure in a manner that is harmful to the contaminant, and aqueous decontamination includes exposing surfaces and/or compartments to a liquid chemical agent harmful to the contaminant. The liquid chemical element may be in atomized form.

Figure 1:
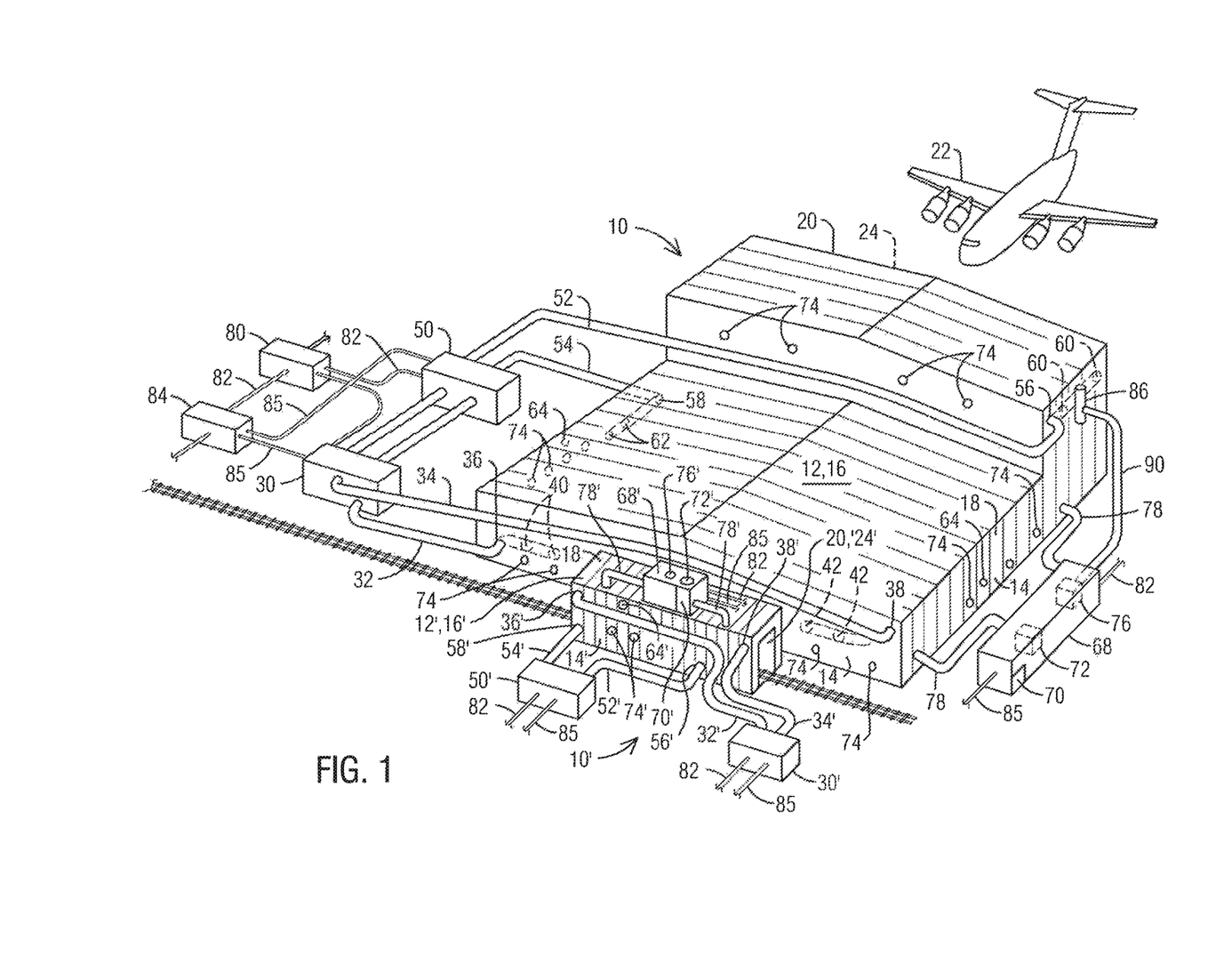
FIG. 1 is a top perspective view of a decontamination system for a transportation asset.

FIG. 1 illustrates a decontamination system 10 embodied as a hangar, including an enclosure 12 having walls 14 and a roof 16, each composed of a plurality of insulated panels 18 assembled together, and an access 20 through which a transportation asset 22, such as a fixed wing or a rotary wing aircraft, may enter and exit an interior 24 of the enclosure 12. Optionally, the insulated panels 18 may be used to form a floor 26 (visible in FIG. 2) of the enclosure. In an exemplary embodiment, the insulated panels 18 forming the floor 26 may be secured together around wheels or other means of supporting a weight of the transportation asset such that the weight of the transportation asset is not imposed on the insulated panels 18. A transportation asset may be any device meant to transport people and/or cargo, including devices with interior compartments meant to house an operator and/or passengers and/or meant to house materials/cargo. The enclosure 12 may be sized to accommodate a range of transportation assets, from large aircraft to automobiles. When so sized, several smaller transportation assets may be disposed in the enclosure 12 at the same time for simultaneous decontamination.

The decontamination system 10 further includes one or more humidifying modules 30 in fluid communication with the interior 24 via a humidifier feed conduit 32, which may also be insulated, and a humidifier return conduit 34 which may likewise be insulated. The humidifier feed conduit 32 may connect to the enclosure 12 at an enclosure humidifier feed port 36 and the humidifier return conduit 34 may connect to the enclosure 12 an enclosure humidifier exhaust port 38. The walls 14 may include a plurality of internal enclosure humidifier feed openings 40 in fluid communication through the walls 14 with the enclosure humidifier feed port 36 to provide several injection points for fresh heated and/or humidified air. The fluid communication may be provided by a passageway through the wall 14 indicated by the dotted lines there between. The walls 14 may include a plurality of internal enclosure humidifier exhaust openings 42 in fluid communication through the walls 14 with the enclosure humidifier exhaust port 38 to provide several exhaust points for spent heated and/or humidified air. The fluid communication may be provided by a passageway through the wall 14 indicated by the dotted lines there between.

The decontamination system 10 further includes a dehumidifying module 50 in fluid communication with the interior 24 via a dehumidifier feed conduit 52, which may also be insulated, and a dehumidifier return conduit 54 which may likewise be insulated. The dehumidifier feed conduit 52 may connect to the enclosure 12 at an enclosure dehumidifier feed port 56 and the dehumidifier return conduit 54 may connect to the enclosure 12 an enclosure dehumidifier exhaust port 58. The walls 14 may include a plurality of internal enclosure dehumidifier feed openings 60 in fluid communication through the walls 14 with the enclosure dehumidifier feed port 56 to provide several injection points for fresh cooled and/or dehumidified air. The fluid communication may be provided by a passageway through the wall 14 indicated by the dotted lines there between. The walls 14 may include a plurality of internal enclosure dehumidifier exhaust openings 62 in fluid communication through the walls 14 with the enclosure dehumidifier exhaust port 58 to provide several exhaust points for spent cooled and/or dehumidified air. The fluid communication may be provided by a passageway through the wall 14 indicated by the dotted lines there between.

The decontamination system 10 may also include enclosure sensors 64 configured to sense one or more environmental conditions within the interior 24 of the enclosure 12, including but not limited to temperature and humidity. In an exemplary embodiment, the temperature sensors are thermocouples, such as T-type thermocouples (Omega® Part Number 5SRTC-TT-T-20-36) with a dynamic range of 32-662 degrees F. and a tolerance of ±1.8 degrees F. In an exemplary embodiment, each temperature sensor within the interior 24 measures an air temperature within the interior 24 and a temperature of a surface of the interior 24 where the sensor is mounted. In an exemplary embodiment there may be temperature sensors inside the asset 22. Each temperature sensor within the asset 22 measures an air temperature within the asset 22 and a temperature of a surface of the asset 22 where the temperature sensor is mounted. In an exemplary embodiment additional temperature and humidity sensors within the interior 24 are positioned along an exterior surface of the asset 22, to measure the temperature and humidity along the exterior surface asset 22. In an exemplary embodiment, the temperature sensors along the exterior surface of the asset 22 measure an air temperature and a temperature of the exterior surface of the asset 22 where the sensors are mounted.

In an exemplary embodiment, the humidity sensors are relative humidity sensors, such as Vaisala® HMT120 Humidity Transmitters with a range of 1-100% relative humidity and an accuracy of ±1.5% at ambient conditions and ±4.0% at high temperature conditions. The degree of humidity may be expressed as relative humidity, which is the ratio of the amount of water vapor in the gas at a specific temperature to the maximum amount that the gas could hold at that temperature. It is expressed as a percentage. A completely saturated gas is said to be at 100% relative humidity, and partial saturation is designated by smaller percentages.

The decontamination system 10 may also include an aqueous decontamination module 68 having an aqueous decontamination module control panel 70, a module reservoir 72 configured to hold a supply of an aqueous disinfectant solution, enclosure nozzles 74 configured to deliver an atomized spray of the aqueous disinfectant solution into the interior 24 of the enclosure 12 (fluid communication path not shown), and a module pump 76 configured to pump the aqueous disinfectant solution from the module reservoir 72 to the enclosure nozzles 74. The module pump 76 may be in fluid communication with the enclosure nozzles 74 via one or more module disinfectant feed lines 78. There may also be a supply 86 of compressed gas, such as air, that is in fluid communication with the enclosure nozzles 74, 74' (fluid communication path not shown) to aid in the atomization of the aqueous disinfectant solution. For example, the compressed air may be in fluid communication with the enclosure nozzles 74, 74' by way of lines through the aqueous decontamination module 68, 68', which permits control of a flow rate of the compressed gas by the aqueous decontamination module 68, 68'. Alternately, each aqueous decontamination module 68, 68' may have its own supply 86 of compressed air. The number of enclosure nozzles 74, 74' and associated plumbing (pipes, tubes etc.) necessary to create the desired mist of aqueous disinfectant solution in the enclosure 12, 12' will depend on the size and shape of the enclosure 12, 12'. For example, when the enclosure 12, 12' is a hanger for a relatively large aircraft, there may be many enclosure nozzles 74, 74' positioned at various perimeter locations, at various heights, and even in the roof 16, 16' if necessary. In an exemplary embodiment the aqueous decontamination module 68 may include an internal controller (not shown) to independently monitor and control the dose of aqueous disinfectant solution in the interior 24. The aqueous decontamination module 68 may be employed for any transportation asset needing aqueous disinfectant solution decontamination. A smaller enclosure 12 may be used for single vehicles such as fire trucks, ambulances etc. A larger enclosure 12 may be used for a fleet of the smaller transportation assets. Alternately, biothermal decontamination may be suitable for a fleet of smaller transportation assets and larger transportation assets.

The decontamination system 10 of FIG. 1 is shown with an optional railcar decontamination system 10' having its own enclosure 12' with walls 14' and a roof 16'. The enclosure 12' may be secured to enclosure 12 or it may stand alone. The enclosure 12' is also composed of insulated panels 18 assembled together, and an access 20' via which a railcar can enter and exit the interior 24' of the enclosure 12'. Similar to the decontamination system 10, the railcar decontamination system 10' may have its own humidifying module 30' with humidifier feed conduit 32' leading to an enclosure humidifier feed port 36', and a humidifier return conduit 34' returning from the enclosure humidifier exhaust port 38', both of which may be insulated. The walls 14' may include a plurality of internal enclosure humidifier feed openings 40' (not shown) in fluid communication through the walls 14' with the enclosure humidifier feed port 36' to provide several injection points for fresh heated and/or humidified air. The walls 14' may include a plurality of internal enclosure humidifier exhaust openings 42' (not shown) in fluid communication through the walls 14' with the enclosure humidifier exhaust port 38' to provide several exhaust points for spent heated and/or humidified air.

Similar to the decontamination system 10, the railcar decontamination system 10' may have its own dehumidifying module 50' with dehumidifier feed conduit 52' leading to an enclosure dehumidifier feed port 56', and a dehumidifier return conduit 54' returning from the enclosure dehumidifier exhaust port 58'. The walls 14' may include a plurality of internal enclosure dehumidifier feed openings 60' (not shown) in fluid communication through the walls 14' with the enclosure dehumidifier feed port 56' to provide several injection points for fresh cooled and/or dehumidified air, both of which may be insulated. The walls 14' may include a plurality of internal enclosure dehumidifier exhaust openings 62' (not shown) in fluid communication through the walls 14' with the enclosure dehumidifier exhaust port 58' to provide several exhaust points for spent heated and/or humidified air.

The railcar decontamination system 10' may also include enclosure sensors 64' configured to sense one or more environmental conditions within the interior 24' of the enclosure 12', including but not limited to temperature and humidity, which is a measure of the amount of moisture present in a gas such as air.

The railcar decontamination system 10' may also include an aqueous decontamination module 68' having an aqueous decontamination module control panel 70', a module reservoir 72' configured to hold a supply of an aqueous disinfectant solution, enclosure nozzles 74' configured to deliver an atomized spray of the aqueous disinfectant solution into the interior 24' of the enclosure 12', and a module pump 76' configured to pump the aqueous disinfectant solution from the module reservoir 72' to the enclosure nozzles 74'. The module pump 76' may be in fluid communication with the enclosure nozzles 74' via one or more module disinfectant feed lines 78'. In an exemplary embodiment the aqueous decontamination module 68' may include an internal controller (not shown) to independently monitor and control the dose of aqueous disinfectant solution in the interior 24'.

While the optional railcar decontamination system 10' is shown with its own humidifying module 30', dehumidifying module 50', and associated components, it is within the scope of the disclosure that an exemplary embodiment of the railcar decontamination system 10' may utilize the humidifying module 30, dehumidifying module 50, and the associated components instead of having separate components. Alternately, or in addition, there may be a retractable wall or no wall between the enclosures 12, 12' such that the decontamination system 10 and the railcar decontamination system 10' may share a common interior 24+24'. In this embodiment the modules 30, 50, 68 would be used to decontaminate the transportation assets including railcars.

The decontamination system 10 may also include a discrete power source 80 such as a generator or it may be connected to an exterior power source (not shown) such as a local power grid. The power source 80 may be connected to any of the modules via power transmission lines 82. There may be a central controller 84 that may be in communication with any sensors and with the power source 80 via signal cables 85 such that the central controller 84 may receive sensory input from the sensors and control any of the modules 30, 50, 68, in accord with the sensory input and/or other programming. For example, the central controller 84 may monitor the temperature and humidity and control the humidifying module 30 to bring the parameters up to a set level from ambient. Ambient temperature may be, for example, about 68° F. to about 72° F. Ambient humidity is the humidity in the absence of a humidifier or a dehumidifier. Upon reaching the desired levels the central controller 84 may control the humidifying module 30 to maintain desired conditions in the enclosure 12 as desired, after which the central controller 84 may engage the dehumidifying module 50 to lower the temperature and humidity to ambient. An example of a central controller 84 that may be used with the decontamination system 10 is an Idec-Microsmart Pentra programmable logic control. Such a controller includes RAM and ROM modules or devices and may have SD card capabilities. In an exemplary embodiment, thermocouple grade extension wire is used to connect the sensors 64 with the central controller 84, to preserve the accuracy of the signal from the sensors 64 over distances.

The central controller 84 may also be programmed to cause the aqueous decontamination module 68 to deliver atomized aqueous disinfectant solution to the interior 24 of the enclosure 12, either in conjunction with the biothermal decontamination, before, or after biothermal decontamination, or without associated biothermal contamination. All of these decontamination processes may be performed via programming contained within a processor in the central controller 84, manually controlled, or a combination of both.

In an exemplary embodiment, to achieve biothermal decontamination the humidifying module 30 is configured to raise a temperature within the interior 24 to a predetermined temperature level and to raise a humidity within the interior 24 to a predetermined humidity level. In an exemplary embodiment, the predetermined temperature level is in a range of 0-200 degrees F. and predetermined humidity level is in a range of 0-100%. After the temperature and the humidity of the interior 24 have reached the predetermined temperature level and the predetermined humidity level, the humidifying module 30 maintains the temperature at the predetermined temperature level and the humidity at the predetermined humidity level for a timed duration, such as 1-7 days, for example. After the humidifying module 30 has maintained the desired humidity and temperature for the timed duration, the dehumidifying module 50 may be controlled to lower the temperature within the interior 24 from the predetermined temperature level to an ambient temperature and to lower the humidity within the interior 24 from the predetermined humidity level to an ambient humidity. To achieve aqueous solution decontamination the aqueous decontamination module 68 may deliver/inject aqueous disinfectant solution into the interior 24 until a predetermined dose of active disinfectant chemical agent or compound exists for a predetermined time. An example dose may be 0.035 ml/ft$^3$, and an example predetermined time may be ten (10) minutes. After the predetermined time the aqueous decontamination module 68 may evacuate the interior 24 until the active disinfectant chemical agent or compound dose drops to a predetermined level for a predetermined time. For example, if hydrogen peroxide is the detected compound the threshold concentration may be 1 ppm and the time duration may be 3 minutes.

Likewise, the central controller 84 may be used to control the modules 30', 50', 68' of the optional railcar decontamination system 10', which may be controlled in the same manner modules 30, 50, 68 are controlled as described above.

Figures 2, 3:
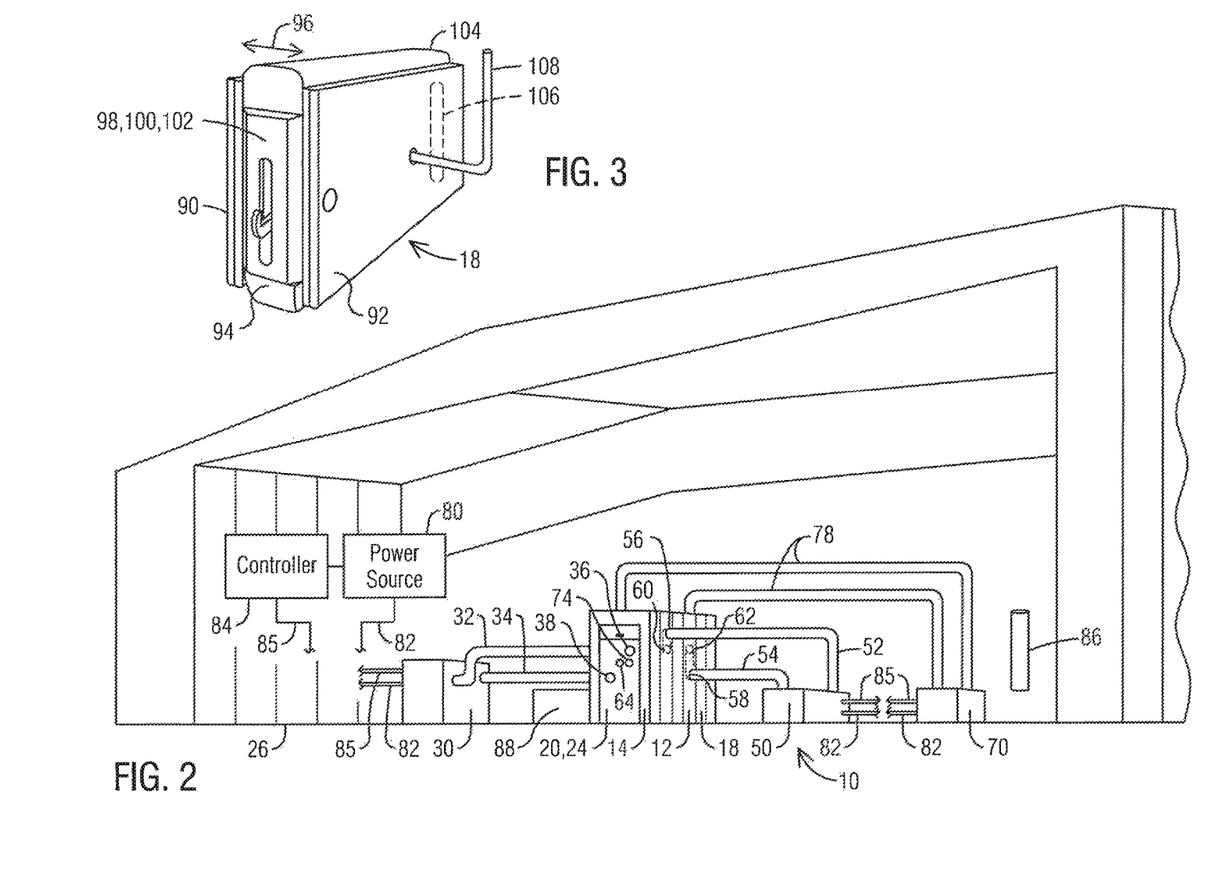
FIG. 2 is a top perspective view of an alternate exemplary embodiment of the decontamination system.
FIG. 3 is a side perspective view of an insulated panel used to form the enclosure of the decontamination system.

FIG. 2 shows an alternate exemplary embodiment where the enclosure 12 and the modules 30, 50, 68 and associated components of the decontamination system 10 are installed within a hangar. The enclosure 12 may be freestanding, or it may have an open side abutted with and sealed to the hangar such that a hanger wall forms part of the enclosure 12. There may be one or several enclosures 12 inside the hangar, and each enclosure may be a standalone in that it may have its own modules 30, 50, 68, or two or more may share modules 30, 50, 68, or there may be a combination of standalone units and sharing units. As shown the access 20 is open (e.g. a roll-up door is rolled up) so that a transportation asset could drive in for decontamination. The supply 86 of compressed gas may likewise be moved inside the hangar. This exemplary embodiment may be operated in the same manners as detailed for the exemplary embodiment of FIG. 1. Further, this exemplary embodiment may or may not be associated with the optional railcar decontamination system 10'. Also visible is an optional storage unit 88 in which items associated with the decontamination systems may be stored. The storage unit 88 may be associated with the enclosure 12 as shown in FIG. 2 such that its contents may be subject to the same decontamination processes available for the enclosure. Alternately, the storage unit 88 may be disposed inside the enclosure 12 in an exemplary embodiment like that shown in FIG. 1 or FIG. 2.

As illustrated in FIG. 3, each insulated panel 18 of the enclosure 12 may include an outer sheet 90 and an inner sheet 92 with an insulating foam layer 94 of a thickness 96 there between. In an exemplary embodiment, the insulating foam layer 94 may be expanded polystyrene, polyurethane or other insulating material. In an exemplary embodiment, the thickness 96 may be in a range of 4-6 inches and the R-value of the insulating foam layer 94 may be in a range of 20-28. The sheets 90, 92 may be made of any metallic, wood or wood composite material, such as powder coated galvanized metal, for example. As further illustrated in FIG. 3, the insulated panels 18 of the enclosure 12 include interlocking mechanisms 98 disposed in the insulating foam layer 94. In the instance of a tongue and groove interlocking mechanism, a first edge 100 of the insulated panel 18 may include a first portion 102 (i.e. the tongue) of the interlocking mechanism 98 and a second edge 104 of the insulated panel 18 may include a second portion 106 (i.e. the groove) of the interlocking mechanism 98. The first portion 102 is configured to secure the first edge 100 to the second edge 104 of a first adjacent panel (not shown). The second portion 106 is configured to secure the second edge 104 to the first edge 100 of a second adjacent panel (not shown). However, any type of interlocking mechanism 98 known to one skilled in the art may be used to detachably secure the insulated panels 18 together, such as a cam lock interlocking mechanism, for example. The interlocking mechanism 98 allows the insulated panels 18 to be detachably secured together and taken apart, optionally with minimal use of a tool 108, in order to facilitate the mobility of the decontamination system 10.

Figure 4:
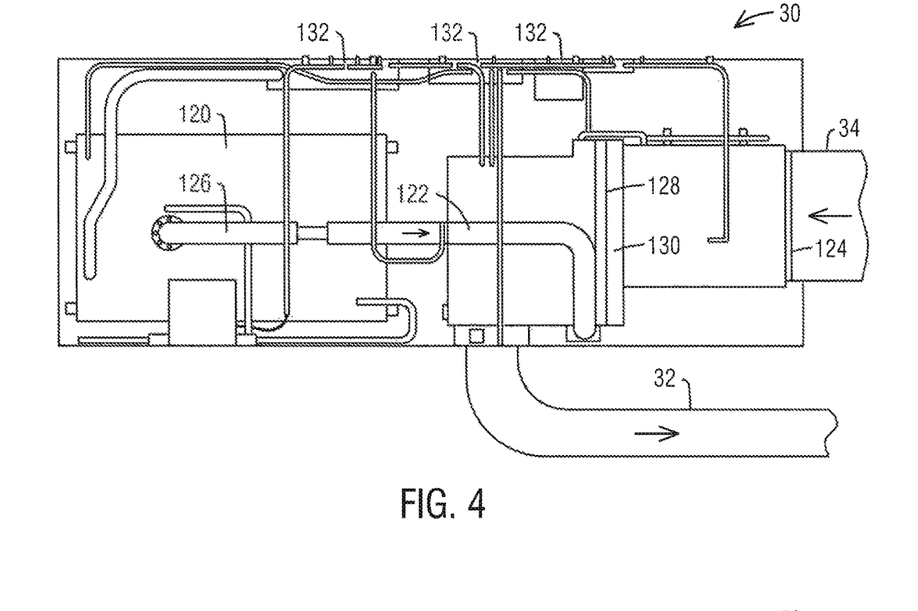
FIG. 4 is a top view of an interior of a humidifying module of the decontamination system of FIG. 1.

FIG. 4 illustrates the components of the humidifying module 30. A boiler 120 is provided in the humidifying module 30 to heat water and generate steam 122 which flows to a blower 124 via humidifier conduit 126. A dispensing coil 128 at the blower 124 is in fluid communication with the boiler 120, to distribute heat from the steam 122 into surrounding air within a heat exchange chamber 130. The blower 124 is provided in fluid flow communication with the heat exchange chamber 130, to direct the heated air from the heat exchange chamber 130 into the humidifier feed conduit 32. Although FIG. 4 depicts the blower 124 connected to one humidifier feed conduit 32, the embodiments of the present invention may include a plurality of portals in the humidifying module 30 to connect the blower 124 to multiple insulated ducts that can be used to direct the heated air to the interior 24. Additionally, in one embodiment a fixture may be provided where one side of the fixture is attached to the humidifier feed conduit 32 and an opposite side of the fixture is attached to a plurality of insulated ducts to split the heated air flow from the humidifier feed conduit 32 into the plurality of insulated ducts. In this embodiment, the plurality of insulated ducts may be connected to a plurality of openings along the surface of the humidifying module 30 to distribute the heated air flow within the interior 24. Alternately, the insulated ducts may be connected to a plurality of respective enclosures 12 to simultaneously heat more than one enclosure 12. A similar fixture may be provided for the humidifier return conduit 34 to unite a plurality of cooled air flows returning from the enclosure 12. The humidifier return conduit 34 is provided in fluid communication with the interior 24 to pass air from the interior 24 to the heat exchange chamber 130 within the humidifying module 30. The returned air is then heated by the dispensing coil 128 before it is pushed back out through the humidifier feed conduit 32 by the blower 124 and back to the interior 24. At least one humidifier control panel 132 controls the operation of the humidifying module 30 and may be in communication with the central controller 84.

Figure 5:
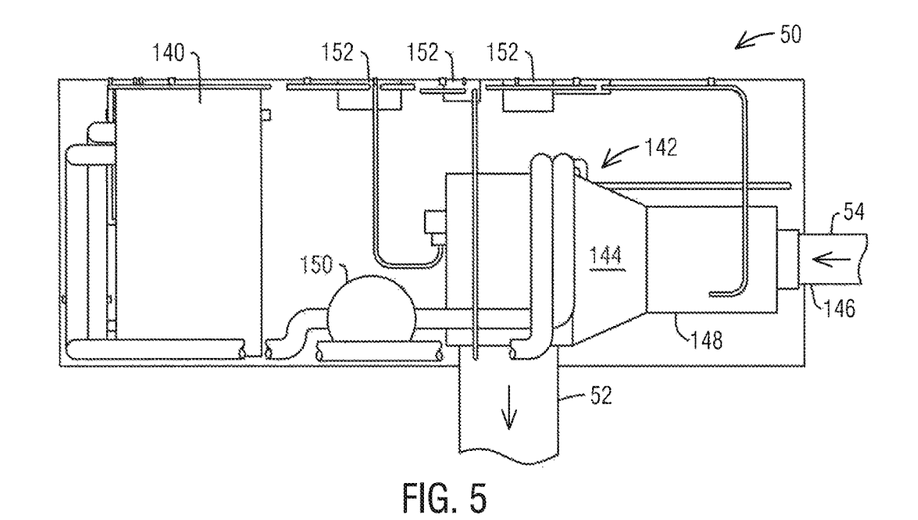
FIG. 5 is a top view of an interior of a dehumidifying module of the decontamination system of FIG. 1.

FIG. 5 shows components of the dehumidifying module 50. The dehumidifying module 50 is in fluid communication with the interior 24 via the dehumidifier feed conduit 52 to direct air from the dehumidifying module 50 to the interior 24. The dehumidifier return conduit 54 returns air from the interior 24 to the dehumidifying module 50. A chiller 140 is provided to cool water within the dehumidifying module 50. A chilling coil 142 in fluid communication with the chiller 140 is positioned in a dehumidifier chamber 144, to cool air within the dehumidifier chamber 144 upon receiving chilled water from the chiller 140. When air returns from the interior 24 through the dehumidifier return conduit 54 to the dehumidifying module 50, it passes through an inlet 146, through a fan 148, over the chilling coil 142 and to the dehumidifier chamber 144, and back into the dehumidifier return conduit 54. Water returned from the chilling coil 142 to the chiller 140 is directed through a pipe that passes through a buffer tank 150, to reduce a temperature of the water before it returns to the chiller 140. At least one dehumidifier control panel 152 controls the operation of the dehumidifying module 50 and may be in communication with the central controller 84.

Figure 6:
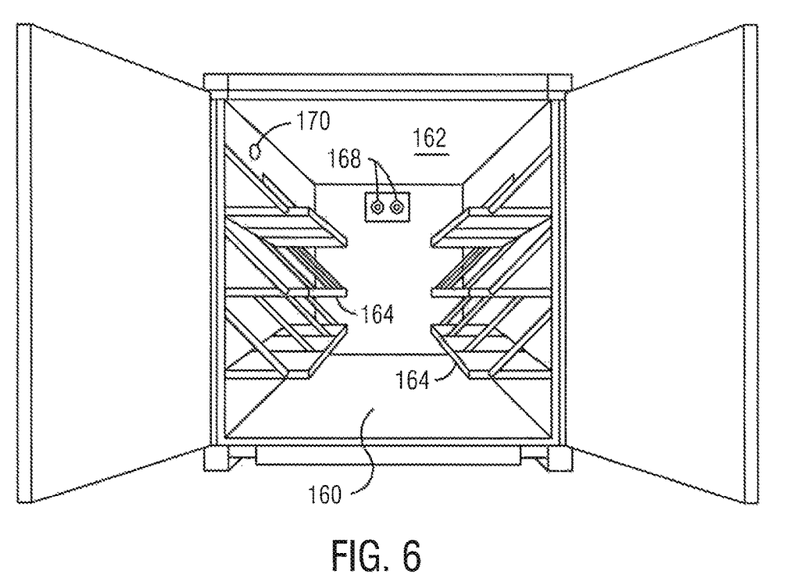
FIGS. 6-7 are respective rear and front views of an exemplary embodiment of the storage and decontamination module of the decontamination system of FIG. 1.

FIG. 6 illustrates an optional, discrete storage and aqueous decontamination module 160. When being used for storage, the humidifier feed conduit 32, the humidifier return conduit 34, the dehumidifier feed conduit 52, and the dehumidifier return conduit 54, as well as other duct fixtures or connectors for the insulated panels 18 or to assemble the enclosure 12 may be stored and transported in a storage/decontamination chamber 162 within the storage and aqueous decontamination module 160. To that end a plurality of shelves 164 are disposed therein, and may be pivotally mounted to an interior surface 166 of the storage/decontamination chamber 162, such that one or more shelves 164 can be pivoted to a horizontal position to hold items.

For instances when a smaller aqueous decontamination chamber may be suitable, or when a different aqueous disinfectant solution is to be used, the storage/decontamination chamber 162 may be used. There may be storage/decontamination nozzles 168 in fluid communication with a reservoir (not shown) configured to inject, optionally in atomized form, the aqueous disinfectant solution into the storage/decontamination chamber 162. There may be storage/decontamination sensors 170 configured to sense one or more environmental conditions within the storage/decontamination chamber 162, including but not limited to temperature and humidity. In an exemplary embodiment the storage/decontamination sensors 170 may be the same as the enclosure nozzles 74.

Figure 7:
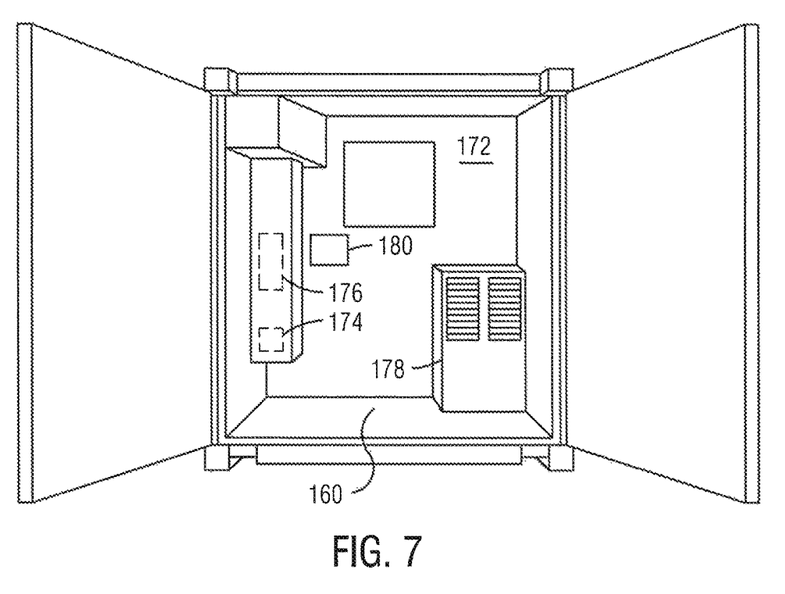

FIG. 7 illustrates a utility region 172 of the storage and aqueous decontamination module 160, including a storage/decontamination reservoir 174 configured to contain a supply of the aqueous disinfectant solution, a storage/decontamination pump 176 configured to deliver the aqueous disinfectant solution from the storage/decontamination reservoir 174 to the storage/decontamination nozzles 168, a storage/decontamination HVAC system 178 configured to move air in and out of the storage/decontamination chamber 162, and a storage/decontamination controller 180 configured to control operation of the various components in the storage and aqueous decontamination module 160. While shown in a separate area, the storage/decontamination reservoir 174, the storage/decontamination pump 176, and the storage/decontamination controller 180 can alternately be positioned inside the storage/decontamination chamber 162.

To achieve aqueous solution decontamination in the discrete storage and aqueous decontamination module 160, storage/decontamination pump 176 may deliver aqueous disinfectant solution into the storage/decontamination chamber 162 until a predetermined dose of aqueous disinfectant solution exists for a predetermined time, after which the storage/decontamination HVAC system 178 may evacuate the storage/decontamination chamber 162 to a predetermined level of aqueous disinfectant solution (such as zero) for a predetermined time.

Figure 8:
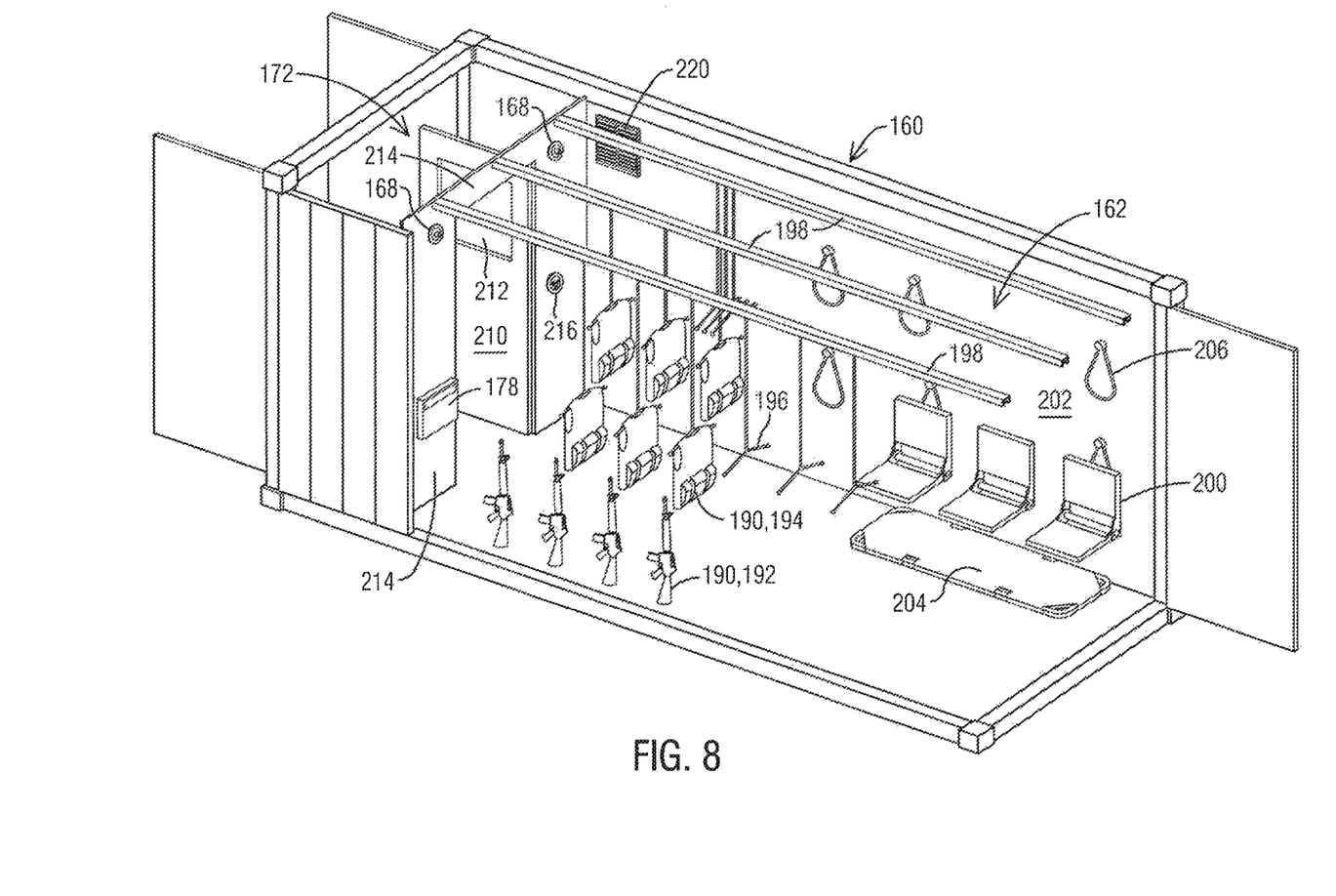
FIGS. 8-9 are respective isometric and end views of an alternate embodiment of the storage and decontamination module of the decontamination system of FIG. 1.
Figure 9:
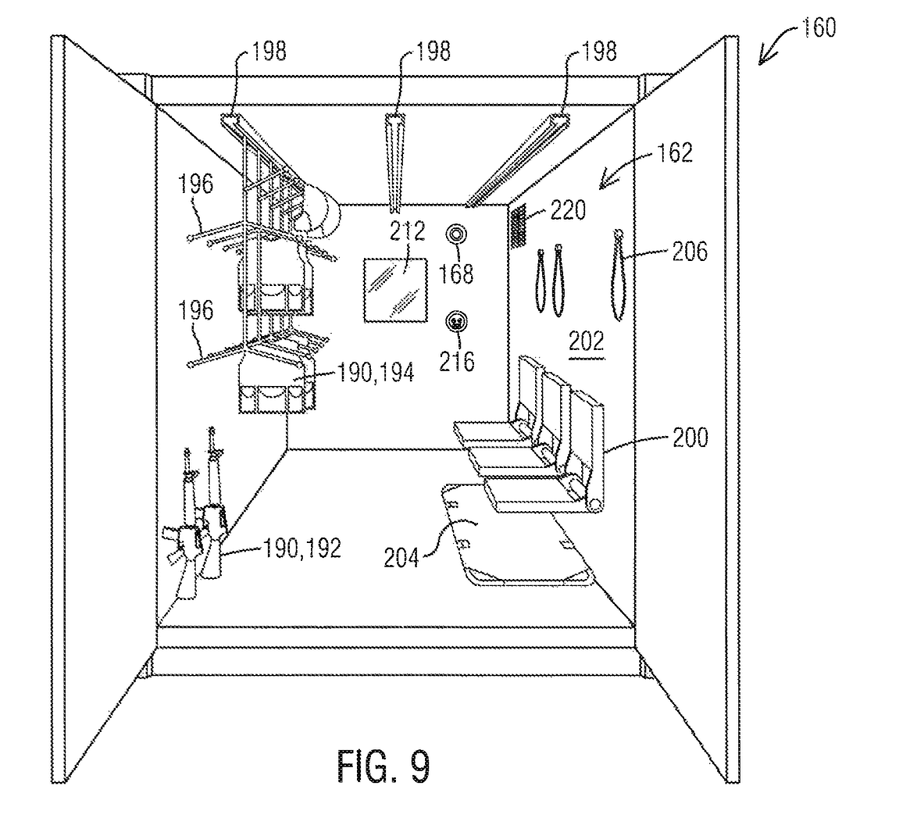

FIGS. 8-9 illustrate an alternate exemplary embodiment of the discrete storage and aqueous decontamination module 160 configured to decontaminate equipment 190 such as weapons 192 and utility vests 194 etc. The equipment 190 may be suspended from gear hangers 196 which may be secured by ceiling mounted hangar tracks 198. In addition, seats 200 may be secured to a wall 202. These seats 200 may fold up to make room, and may fold down to provide a place for individuals who may also need to be decontaminated. This is possible when certain aqueous decontaminants are used at a relatively low concentration, such as chlorine dioxide. However, appropriate respiration protection is recommended for individuals being decontaminated. A stretcher 204 may be provided for an incapacitated individual needing to be decontaminated. Support cabling 206 may also be secured to the wall 202 to aid those individuals who need to be decontaminated. There may be a door 210 with an optional viewing window 212 through a utility wall 214 between the storage/decontamination chamber 162 and the utility region 172 of the storage and aqueous decontamination module 160. The storage/decontamination nozzles 168 may be located on the utility wall 214 to simplify fluid communication with the utility region 172. There may be a decontamination port 216 and an exhaust vent 220 to provide exhaust for the storage/decontamination chamber 162. The discrete storage and aqueous decontamination module 160 may perform any of the decontamination modes that the decontamination system 10 performs, including humidification, dehumidification, aqueous disinfection (injection), and aeration as detailed below.

The aqueous disinfectant solution used in either or both the enclosure 12 and the storage/decontamination chamber 162 may include hydrogen peroxide, chlorine based compounds such as chlorine dioxide and/or hypochlorite, quarternary ammonium compounds, glutaraldehyde, formaldehyde, etc. By way of example, the disinfectant solution may include an aqueous hydrogen peroxide solution that contains about 5% by volume to about 20% by volume of hydrogen peroxide. More preferably, the solution contains about 8% by volume of hydrogen peroxide. In another embodiment, the disinfectant solution is an aqueous chlorine dioxide solution. For example, the disinfectant solution may be 0.2% by weight aqueous chlorine dioxide solution. More specifically, the solution may comprise 0.2 wt % oxychlorine compounds, 0.125 wt % n-alkyl dimethyl benzyl ammonium chloride, 0.125 wt % n-alkyl ethylbenzyl ammonium chloride, and the remaining 99.55 wt % being inert ingredients.

Any or all of the humidifying module 30, the dehumidifying module 50, the aqueous decontamination module 68, the storage and aqueous decontamination module 160, the power source 80, and the central controller 84, may be housed in its own discrete container. The container may be modular, and may be an intermodal shipping container made to relevant International Organization for Standardization (ISO) standards, such as a CONEX™ box. Each module may be transportable using various transportation modes such as air, rail or ground transportation. Alternately, components of any or all of the humidifying module 30, the dehumidifying module 50, the aqueous decontamination module 68, the storage and aqueous decontamination module 160, the power source 80, and the central controller 84, may be spread over more than one discrete container.

Figure 10:
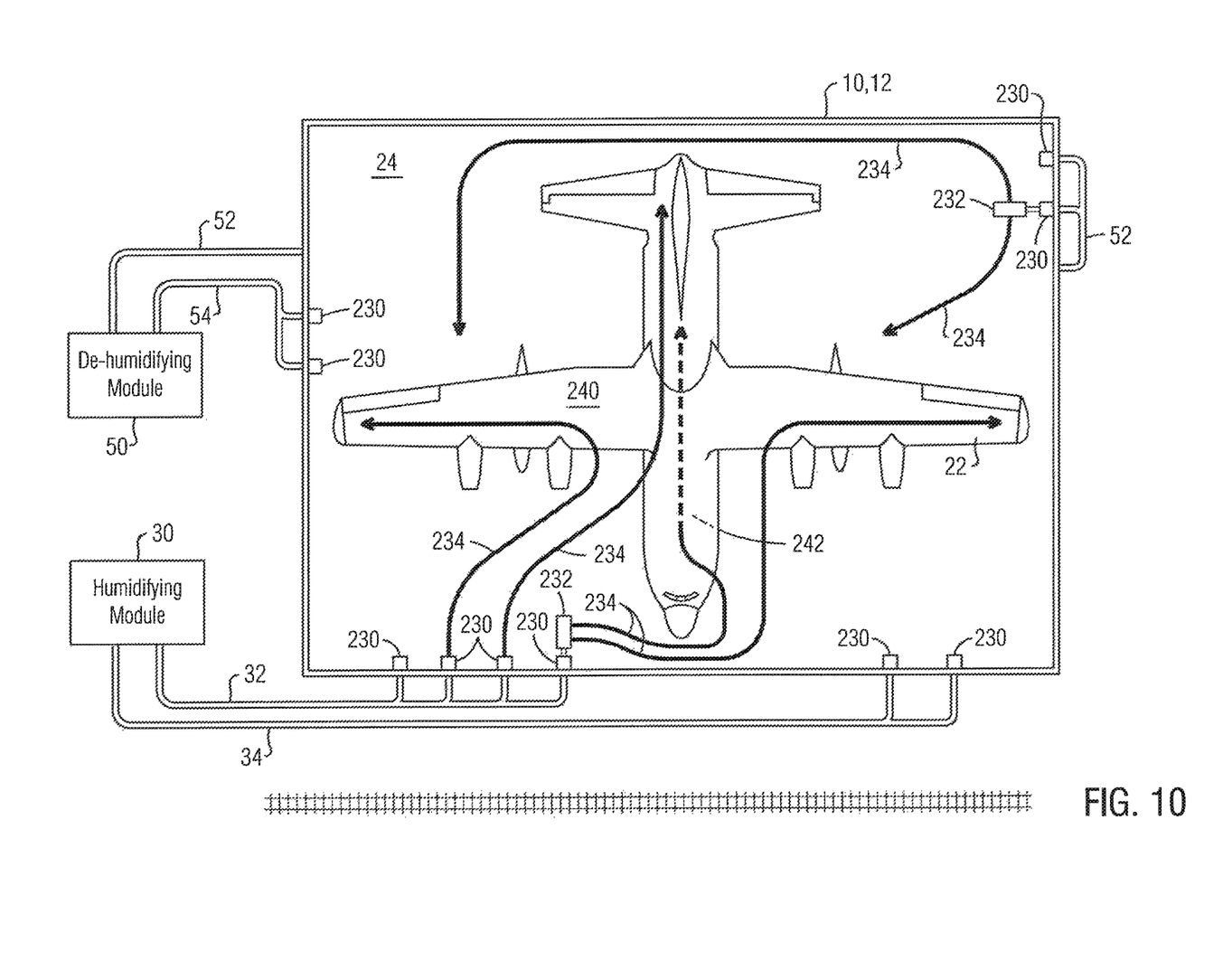
FIG. 10 is a top view of the interior of the decontamination system of FIG. 1.

FIG. 10 is a top view of the interior 24 of the decontamination system 10. In order to illustrate an exemplary embodiment of fluid distribution within the interior 24, only components to the fluid distribution are shown for clarity. In this exemplary embodiment the humidifying module 30 delivers humidifier-treated air to the interior 24 directly through the wall to respective connectors 230. In this exemplary embodiment the air from the interior 24 is returned to the humidifying module 30 via the connectors 230 that connect directly through the wall to the humidifier return conduit 34. Interior ducts 234 that may be insulated may optionally be connected to the connectors 230 to distribute the humidifier-treated air directly to the asset 22. Splitters 232 may optionally be secured to the connectors 230 to permit attachment of multiple interior ducts 234 to one connector 230. This may be in addition to or in lieu of delivering humidifier-treated air directly to the interior 24 without interior ducts 234. The interior ducts 234 may be routed to locations proximate an exterior 240 of the asset 22. In such a case the interior ducts 234 may further include openings such that the interior duct 234 becomes a plenum that delivers humidifier-treated air along the exterior 240 of the asset 22. Alternately, or in addition, the interior ducts 234 may be routed to an interior 242 of the asset 22, and inside the asset 22 the interior ducts 234 may optionally have additional holes such that the portion of the interior duct 234 inside the asset 22 acts like a plenum, delivering humidifier-treated air along the interior of the asset 22.

In this exemplary embodiment the dehumidifying module 50 delivers dehumidifier-treated air to the interior 24 via the dehumidifier feed conduit 52 that leads directly through the wall to respective connectors 230. In this exemplary embodiment air from the interior 24 is returned to the dehumidifying module 50 via the connectors 230 that connect directly through the wall to the dehumidifier return conduit 54. Interior ducts 234 that may be insulated may optionally be connected to the connectors 230 to distribute the dehumidifier-treated air directly to the asset 22. Splitters 232 may optionally be secured to the connectors 230 to permit attachment of multiple interior ducts 234 to one connector 230. This may be in addition to or in lieu of delivering dehumidifier-treated air directly to the interior 24 connectors 230. The interior ducts 234 may likewise be routed to locations proximate the exterior 240 of the asset 22. In such a case the interior ducts 234 may further include openings such that the interior duct 234 becomes a plenum that delivers dehumidifier-treated air along the exterior 240 of the asset 22. Alternately, or in addition, the interior ducts 234 may be routed to an interior 242 of the asset 22, and inside the asset 22 the interior ducts 234 may optionally have additional holes such that the portion of the interior duct 234 inside the asset 22 acts like a plenum, delivering dehumidifier-treated air along the interior of the asset 22.

The interior ducts 234 may be used, for example, when the asset 22 is relatively small compared to a volume of the interior 24, where it would be more efficient to deliver treated air directly to the asset as opposed to the entire volume of the interior 24. If the asset 22 is relatively large the interior ducts 234 may be used or they may not. Alternately, only some of the interior ducts 234 may be used, such as those which deliver treated air to the interior 242 of the asset 22. Alternately, for an asset 22 that occupies a relatively large volume of the interior 24, one may just open the doors to the asset 22 and decontaminate/process without the need for interior ducts 234 that lead to the interior 242 of the asset 22. If an interior duct 234 is not used then any treatment air will flow into the enclosure 24 directly through the connectors 230 to which no interior ducts 234 are connected. Any and all combinations are within intended scope of this disclosure.

Figure 11:
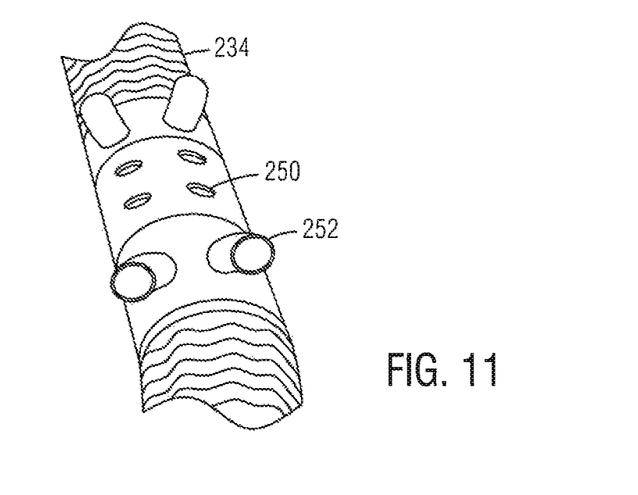
FIG. 11 is a perspective view of an insulated duct of the decontamination system of FIG. 10.

FIG. 11 depicts an exemplary embodiment of an interior duct 234 that is insulated and includes openings 250 and vents 252 along a length of the interior duct 234. In an exemplary embodiment the interior duct 234 has a diameter that may vary depending on a location and of the openings 250 and vents 252, and a volume of air that passes there through. For example, the diameter may be largest at an inlet of the interior duct 234 and decrease along a direction of the flow therein. An example inlet diameter may be twenty inches, and this may decrease to twelve or eight inches downstream.

In order to commence a biothermal decontamination operation an operator enters one or more parameters associated with a decontamination mode into the central controller 84, such as the timed duration, the predetermined temperature level, and the predetermined humidity level. The central controller 84 then transmits a signal to the humidifier control panels 132 to activate the boiler 120 until the heated air passed through the humidifier feed conduit 32 and into the interior 24 causes the temperature to reach the predetermined temperature level and the humidity to reach the predetermined humidity level. In an embodiment the humidifying module 30 may be equipped with an electrical resistance heater to initially heat air introduced into the interior 24, before steam is injected into the interior 24 to prevent potential condensation.

During this process, the central controller 84 continuously monitors the temperature and humidity measurements from the enclosure sensors 64 in the interior 24. The enclosure sensors 64 may be wired or wireless sensors, for example. To that end the temperature of the air at the humidifier feed conduit 32 and the air at the humidifier return conduit 34 may be monitored to determine a point in time when to initiate a start time of a decontamination mode. As these temperatures converge and are compared to the temperature of the interior 24, the timing of the decontamination mode may be initiated when the difference in supply temperature and return temperature are within an acceptable range for a predetermined time and/or the temperature within the enclosure is at or within a temperature range for a predetermined time.

After the central controller 84 receives sensor data that the temperature and the humidity measurements within the interior 24 are at the predetermined temperature level and predetermined humidity level, the central controller 84 selectively transmits a signal to the humidifier control panels 132, to control the boiler 120 in order to maintain the predetermined temperature level and predetermined humidity level within the interior 24 for the timed duration. During the timed duration for decontamination, the central controller 84 continuously monitors the enclosure sensors 64 within the interior 24 and selectively transmits the signals to the humidifier control panels 132. For example, if the temperature and the humidity fall below the predetermined temperature level and the predetermined humidity level, the central controller 84 transmits a signal to the humidifier control panels 132 to control the boiler 120 to increase the temperature and the humidity to the respective predetermined temperature level and predetermined humidity level. Although FIG. 1 depicts that the central controller 84 is positioned external to the modules 30, 50, 68, the embodiments of the present invention may provide that the central controller 84 is positioned in one of the modules 30, 50, 68, for example. In another embodiment, the humidifying module 30 may include an internal controller (not shown) to independently monitor the temperature and humidity data from the enclosure sensors 64 within the interior 24 and activate the boiler 120, for example.

After the timed duration associated with decontamination mode has elapsed, the central controller 84 transmits one or more signals to the humidifier control panels 132 to cease heating and humidifying the air, to the dehumidifier control panels 152 to activate the chiller 140 until the cooled air passed through the dehumidifier feed conduit 52 and into the interior 24 causing the temperature to lower from the predetermined temperature level to an ambient temperature and the humidity to lower from the predetermined humidity level to an ambient humidity within the interior 24. During this process, the central controller 84 continuously monitors the enclosure sensors 64 within the interior 24 and continuously activates the chiller 140 until the temperature and the humidity within the interior 24 are at the ambient levels.

In addition, the temperature of air supplied to the interior 24 from the dehumidifying module 50 and the temperature of the air returned to the dehumidifying module 50 may be monitored. As these temperatures converge and are compared to the temperature of the interior 24 the timing of the dehumidifying mode may be initiated when the difference in supply temperature and return temperature are within an acceptable range for a predetermined time and/or the temperature within the interior 24 is at or within a temperature range for a predetermined time. That is, the dehumidification mode may be held for a predetermined time at a predetermined ambient temperature as well as a predetermined humidity level.

In an exemplary embodiment, the central controller 84 transmits the signals to the dehumidifier control panels 152 over a minimum time period, such that the chiller 140 decreases the temperature and the humidity within the interior 24 to the ambient levels over the minimum time period, to prevent condensation from forming over the transportation asset's interior and exterior surfaces. In one example, the volume of the interior 24 may be in a range of 10,000-6,000,000 cu ft. and the minimum time period may be in a range of 120-28,800 minutes. When the operator wants to commence decontamination the operator may enter the minimum time period parameter into the central controller 84, in addition to the other parameters associated with the decontamination mode discussed above. Although FIG. 1 depicts that the central controller 84 is positioned external to the modules 30, 50, 68, in another embodiment the dehumidifying module 50 may include an internal controller (not shown) to independently monitor the temperature and humidity within the interior 24 and selectively activate the chiller 140, for example. The internal controller within the dehumidifying module 50 may be in communication with an internal controller (not shown) within the humidifying module 30 through one or more Ethernet cables 182. In this embodiment, the user inputs the parameters of decontamination at the internal controller within the humidifying module 30. The internal controller within the humidifying module 30 then selectively activates the boiler 120, such that the temperature and the humidity within the interior 24 are raised to the predetermined temperature level and the predetermined humidity level for the timed duration. The internal controller within the humidifying module 30 then transmits a signal through the Ethernet cables 182 to the internal controller within the dehumidifying module 50, to selectively activate the chiller 140, until the temperature and the humidity within the interior 24 is lowered from the predetermined temperature level and the predetermined humidity level to ambient levels over the minimum time period.

In order to commence aqueous decontamination the operator enters one or more parameters associated with a decontamination mode into the central controller 84, such as the time duration and the predetermined dose of the active disinfectant chemical agent or compound. The central controller 84 then transmits a signal to the aqueous decontamination module control panel 70 to activate the module pump 76 to pump aqueous disinfectant solution from the module reservoir 72, through the module disinfectant feed lines 78, and through the enclosure nozzles 74, where the aqueous disinfectant solution is atomized and delivered into the enclosure. The enclosure sensors 64 may monitor a dose of the active disinfectant chemical agent or compound and the process continues until a threshold level is reached, at which point the central controller 84 will stop the module pump 76, stopping delivery of the aqueous disinfectant solution. The central controller 84 may continue to monitor the dose of the active disinfectant chemical agent or compound in the interior 24 via the enclosure sensors 64 and if the dose drops below the threshold level, the central controller 84 will activate the module pump 76 and deliver more aqueous disinfectant solution until the threshold level is again reached. This process may continue until the predetermined time passes, or until the operator dictates. After the predetermined time passes, any remaining active disinfectant chemical agent or compound may be evacuated during an aeration mode by an evacuation system (not shown), allowed to settle, or the enclosure 12 may be opened/vented to permit the active disinfectant chemical agent or compound doses to drop to the desired level. For example, if hydrogen peroxide is the detected compound the threshold concentration may be 1 ppm and the time duration may be 3 minutes. In another exemplary embodiment the aqueous decontamination module control panel 70 may include an internal controller (not shown) to independently monitor and control the dose of aqueous disinfectant in the enclosure 12. Alternately, aqueous disinfectant solution may be injected for periods of time separate by dwell times when no injection takes place. Injection time is determined by cubic feet of within the enclosure. Dwell time is determined/defined as the difference between a total exposure time necessary to kill the designated pathogen minus the total injection time.

Decontamination of the discrete storage and aqueous decontamination module 160 may be accomplished using the storage/decontamination controller 180, which may be equipped with a touch-screen. The storage/decontamination controller 180 is in signal communication with the storage/decontamination pump 176 and the storage/decontamination reservoir 174 to activate the storage/decontamination pump 176 and deliver the aqueous disinfectant solution to the storage/decontamination nozzles 168 so that the aqueous disinfectant solution is dispersed in an atomized form in the storage/decontamination chamber 162. The time duration that the aqueous disinfectant solution is dispersed through the storage/decontamination nozzles 168 may vary according to the volume of the storage/decontamination chamber 162 and the volume of aqueous disinfectant solution needed to decontaminate the storage/decontamination chamber 162. To that end, the dispersal of the aqueous disinfectant solution through the storage/decontamination nozzles 168 may be divided into discrete timed periods including one or more dwell times during which no aqueous disinfectant solution is injected interposed between two injection periods. By way of example, an injection may be made continuously for 4 minutes for a first injection period followed by a 2 minute first dwell time, which is then followed by a second 4 minute injection period followed by a second 2 minute dwell time for an injection phase lasting 12 minutes.

After the injection mode has been completed, an aeration mode is initiated by the storage/decontamination controller 180 transmitting one or more signals to activate the storage/decontamination HVAC system 178. During the aeration mode, the storage/decontamination sensor 170 within the storage/decontamination chamber 162 detects the dose of the active disinfectant chemical agent or compound within the storage/decontamination chamber 162 and transmits this data to the storage/decontamination controller 180. The storage/decontamination controller 180 may be programmed such that once the dose of the detected aqueous decontamination solution has dropped to a predetermined threshold for a predetermined time duration, signals are generated to turn off the storage/decontamination HVAC system 178. For example, if hydrogen peroxide is the detected compound the threshold concentration may be 1 ppm and the time duration may be 3 minutes. When a decontamination operation of the storage/decontamination chamber 162 is completed, the storage/decontamination controller 180 touchscreen may be configured to display an amount of the aqueous disinfectant solution used and an amount of the aqueous disinfectant solution remaining in the storage/decontamination reservoir 174. Although the embodiment of the storage and aqueous decontamination module 160 depicted has a storage/decontamination controller 180 that is internally disposed, the storage and aqueous decontamination module 160 may alternately be controlled by the central controller 84. In another exemplary embodiment, the storage and aqueous decontamination module 160 may be controlled by the central controller 84. In an exemplary embodiment, the storage and aqueous decontamination module 160 may be a discrete, independently operable system such that it need not be associated with the components needed for biothermal decontamination.

Any number of containers may be used per module, any or all may be programmable, any combination of modules may compose the decontamination system 10, and central control, decentralized control, or a combination of central and decentralized control as well as manual control, automated control, or a combination of manual and automated control may be employed as desired.

A method of decontamination includes assembling the plurality of insulated panels 18 to form the enclosure 12. The enclosure 12 is then connected to the humidifying module 30, via the humidifier feed conduit 32 and the humidifier return conduit 34, the dehumidifying module 50 via the dehumidifier feed conduit 52 and the dehumidifier return conduit 54, and the aqueous decontamination module 68 via the module disinfectant feed lines 78. The humidifying module 30 raises the temperature and humidity within the enclosure 12 to the predetermined temperature level and the predetermined humidity level for the timed duration. The dehumidifying module 50 then lowers the temperature and humidity within the enclosure 12 to the predetermined temperature level and the predetermined humidity level for a predetermined time. Alternately, or in addition, the aqueous decontamination module 68 may deliver aqueous disinfectant solution into the interior 24 until a predetermined dose of active disinfectant chemical agent or compound exists for a predetermined time, after which the aqueous decontamination module 68 may evacuate the interior 24 until the active disinfectant chemical agent or compound dose drops to a predetermined level for a predetermine time. When either or both of the biothermal decontamination and the aqueous solution decontamination are complete the process is complete until initiated again.

While the preferred embodiments of the present invention have been shown and described herein, it will be obvious that such embodiments are provided by way of example only. Numerous variations, changes and substitutions will occur to those of skill in the art without departing from the invention herein. Non-limiting examples include a component that is described above as being attached to one part of the apparatus may alternatively be attached to a different part of the apparatus in other embodiments. Parts described as being indirectly connected may be connected directly to each other, and vice versa. Component parts may be assembled from individual pieces or may be integrally formed as a single unit. Alternative types of connectors and alternative materials may be used. The apparatus may be used with other types of power tools. Accordingly, it is intended that the invention be limited only by the spirit and scope of the appended claims.

What is claimed is:

1. A decontamination system, comprising:
a plurality of interconnected and insulated panels configured to form a wall and a roof and to define an interior of an enclosure configured to enclose a transportation asset;
a humidifying module in fluid communication with the interior of the enclosure and configured to raise a temperature and a humidity of the interior of the enclosure to a predetermined temperature level and a predetermined humidity level for a timed duration, wherein the humidifying module is external relative to the interior of the enclosure;
at least one insulated conduit providing fluid flow communication between the humidifying module and the interior of the enclosure via at least one first opening in the enclosure;
a dehumidifying module in fluid communication with the interior of the enclosure and configured to lower the temperature and the humidity of the interior of the enclosure from the predetermined temperature level and the predetermined humidity level to ambient levels, wherein the dehumidifying module is external relative to the interior of the enclosure; and,
at least one insulated conduit providing fluid flow communication between the dehumidifying module and the interior of the enclosure via at least one second opening in the enclosure.

2. The system of claim 1, further comprising:
a reservoir configured to contain a disinfectant solution;
a pump in fluid communication with the reservoir;
a plurality of enclosure nozzles, each in fluid communication with the pump and configured to disperse the disinfectant solution in atomized form into the interior of the enclosure; and
a programmable controller in signal communication with the at least one pump to activate the at least one pump to deliver the disinfectant solution to the plurality of enclosure nozzles.

3. The system of claim 1, wherein the humidifying module and the dehumidifying module are discrete modules.

4. The system of claim 3, wherein the humidifying module comprises an intermodal shipping container configured to house a boiler, a dispensing coil, and a humidifier blower.

5. The system of claim 3, wherein the dehumidifying module comprises an intermodal shipping container configured to house a chiller, a chilling coil, and a dehumidifier blower.

6. The system of claim 1, wherein the insulated panels exhibit an R-value of at least 20.

7. The system of claim 1, wherein each insulated panel comprises an inner sheet and an outer sheet separated by a layer of insulation, a first portion of an interlocking mechanism disposed in the layer of insulation and configured to secure a first edge of the insulated panel to an edge of a first adjacent interlocking panel, and a second portion of an interlocking mechanism disposed in the layer of insulation and configured to secure a second edge of the insulated panel to an edge of a second adjacent interlocking panel.

8. The system of claim 1, wherein the insulated panels forming the wall comprise an enclosure humidifier port in fluid communication with the humidifying module and a plurality of internal enclosure openings in fluid communication through the wall with the enclosure humidifier port.

9. The system of claim 1, further comprising a framework configured to secure the wall and the roof in a positional relationship with each other.

10. The system of claim 1, further comprising a discrete storage and decontamination module comprising an intermodal shipping container configured to house: a storage/decontamination chamber; a storage/decontamination chamber reservoir configured to contain a disinfectant solution; a storage/decontamination pump; and a storage/decontamination chamber nozzle in fluid communication with the storage/decontamination chamber reservoir and configured to disperse the disinfectant solution in atomized form into the storage/decontamination chamber.

11. The system of claim 1, wherein the enclosure comprises an open side configured to abut and seal against a wall of a discrete structure.

12. The system of claim 1, further comprising an access configured to permit entry of a transportation asset comprising an operator compartment.

13. The system of claim 1, further comprising:
an enclosure sensor configured to monitor an environmental parameter in the interior of the enclosure; and
a central controller in signal communication with the enclosure sensor and configured to control at least one of the humidifying module and the dehumidifying module in response to the environmental parameter.

14. A decontamination system, comprising:
an enclosure sized to enclose an aircraft and comprising a plurality of interconnected and insulated panels that define wall and a roof of the enclosure;
a humidifying module in fluid communication with an interior of the enclosure;

a dehumidifying module in fluid communication with the interior of the enclosure;

an aqueous decontamination module comprising a reservoir configured to contain a disinfectant solution, nozzles in fluid communication with the interior, and a pump configured to provide fluid communication between the reservoir and the nozzles; and a programmable controller configured to control the humidifying module, the dehumidifying module, and the aqueous decontamination module.

15. The system of claim 14, wherein the nozzles are disposed in the wall.

16. The system of claim 14, further comprising insulated interior ducts disposed in the interior, in fluid communication with at least one of the humidifying module and the dehumidifying module, and routed from the wall to the aircraft.

17. The system of claim 16, wherein at least one of the insulated interior ducts forms a plenum that provides fluid communication between the aircraft and the at least one of the humidifying module and the dehumidifying module along a length of the at least one of the insulated interior ducts.

18. The system of claim 14, further comprising a discrete storage and decontamination module comprising an intermodal shipping container configured to house: a storage/decontamination chamber; a storage/decontamination chamber reservoir configured to contain a disinfectant solution; a storage/decontamination pump; and a storage/decontamination chamber nozzle in fluid communication with the storage/decontamination chamber reservoir and configured to disperse the disinfectant solution in atomized form into the storage/decontamination chamber.

19. The system of claim 18, the storage/decontamination chamber further comprising gear racks and seating.

20. The system of claim 14, further comprising a railcar decontamination system comprising:

a railcar enclosure configured to receive a railcar on railroad tracks and comprising a plurality of the interconnected and insulated panels;

wherein the enclosure is in fluid communication with at least one of a railcar humidifying module and the humidifying module, wherein the enclosure is in fluid communication with at least one of a railcar dehumidifying module and the dehumidifying module, and wherein the enclosure is in fluid communication with at least one of a railcar aqueous decontamination module and the aqueous decontamination module.

* * * * *